United States Patent [19]

Mohrmann et al.

[11] Patent Number: 4,992,565
[45] Date of Patent: * Feb. 12, 1991

[54] PREPARATION OF OXIRANES

[75] Inventors: Karl H. Mohrmann; Wolf Reiser, both of Wuppertal, Fed. Rep. of Germany; Siegfried W. Linke, Seoul, Rep. of Korea; Rudolf Zerbes, Wuppertal, Fed. Rep. of Germany

[73] Assignee: Bayer Aktiengesellschaft, Leverkusen, Fed. Rep. of Germany

[*] Notice: The portion of the term of this patent subsequent to Dec. 30, 2003 has been disclaimed.

[21] Appl. No.: 512,612

[22] Filed: Apr. 12, 1990

Related U.S. Application Data

[63] Continuation of Ser. No. 258,912, Oct. 17, 1988 abandoned which is a continuation of Ser. No. 598,562, Apr. 10, 1984 abandoned.

[30] Foreign Application Priority Data

Apr. 29, 1983 [DE] Fed. Rep. of Germany ....... 3315510

[51] Int. Cl.$^5$ .......................................... C07D 301/02
[52] U.S. Cl. .................................................. 549/519
[58] Field of Search ........................................ 549/519

[56] References Cited

U.S. PATENT DOCUMENTS 4,632,999 12/1986 Zerbes et al. ...................... 549/519

FOREIGN PATENT DOCUMENTS 40345 11/1981 European Pat. Off. .
614201 11/1979 Switzerland .

OTHER PUBLICATIONS

V. Franzen, et al., Chem. Ber., "Reaction at Sulfonium Glides with Polar Double Bonds", 96, pp. 1881–1890, (1963).
R. Munauver, et al., Kenya Journal of Science and Technology (A), "The Preparation of Trimethylsulphonium Bromide . . . ", 1 pp. 111–115, (1980).
E. J. Coreg et al., (Corey I), J. Am. Chem. Soc., "Dimethyloxosulfonium Methylide . . . ", 87, pp. 1353–1364, (1965).

E. J. Corey, et al., (Corey II), J. Am. Chem. Soc., "Dimethylsulfonium Methylide . . . ", 84, pp. 3782–3783, (1962).
J. March, "Adv. Org. Chemistry", 2nd Ed., pp. 884–885, McGraw-Hill Book Co., New York (1977).

Primary Examiner—Richard L. Raymond
Assistant Examiner—Mark W. Russell
Attorney, Agent, or Firm—Sprung Horn Kramer & Woods

[57] ABSTRACT

A process for the preparation of an oxirane of the formula

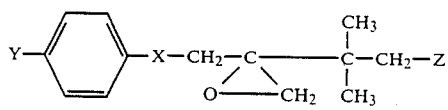

in which
Y is chlorine or phenyl,
X is oxygen or $CH_2$, and
Z is hydrogen or halogen, comprising reacting dimethyl sulphide with methyl bromide in the presence of an inert organic diluent thereby to produce trimethylsulphonium bromide of the formula

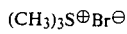

and reacting the trimethylsulphonium bromide with a ketone of the formula

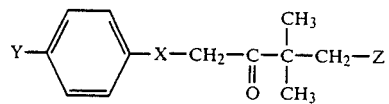

in the presence of a base and in the presence of an inert organic diluent, at a temperature between about 0° C. and 60° C. The end products are produced in high yield and are known intermediates for known fungicides.

9 Claims, No Drawings

PREPARATION OF OXIRANES

This application is a continuation of application Ser. No. 258,912 filed Oct. 17, 1988 now abandoned which is a continuation of Ser. No. 598,562 filed Apr. 10, 1984 now abandoned.

The present invention relates to a new process for the preparation of known oxiranes which can be used as intermediates for the synthesis of compounds having plant-growth regulating and fungicidal activity.

It has already been disclosed that oxiranes can be prepared by reacting dimethyl sulphide with methyl bromide and then reacting the trimethylsulphonium bromide produced thereby with carbonyl compounds in the presence of an inert organic solvent and in the presence of a strong base, such as sodium hydride, sodium amide or potassium tert.-butylate (compare Ber. 96, 1881–1890 (1963)).

It has also been disclosed that 2-(4-chlorophenylethyl)-2-tert.-butyloxirane can be prepared by reacting the trimethylsulphonium methyl sulphate, which is prepared from dimethyl sulphide and dimethyl sulphate, with 1-(4-chlorophenyl)-4,4-dimethyl-3-pentanone in acetonitrile in the presence of sodium methylate (compare EP-OS (European Published Specification) 40,345). The yields in this process are good but, nevertheless, are not always adequate for practical purposes.

It has now been found that the known oxiranes of the formula

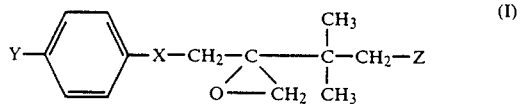

in which
Y represents chlorine or phenyl,
X represents oxygen or CH$_2$ and
Z represents hydrogen or halogen, are obtained when dimethyl sulphide is treated with methyl bromide in the presence of an inert organic diluent, and the trimethylsulphonium bromide, which is produced thereby, of the formula

is reacted with a ketone of the formula

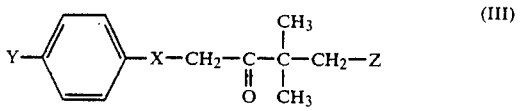

in which
X, Y and Z have the meanings indicated above, in the presence of a base and in the presence of an inert organic diluent at temperatures between 0° C. and 60° C.

It has to be denoted extremely surprising that oxiranes of the formula (I), for example 2-(4-chlorophenylethyl)-2-tert.-butyloxirane, can be prepared by the process according to the invention in higher yields than by the processes hitherto known in which dimethyl sulphide and dimethyl sulphate were used as the starting materials.

The process according to the invention has a number of advantages. Thus, it makes possible the preparation of oxiranes of the formula (I) in very high yields. Moreover, the starting materials are relatively reasonably priced and available on an industrial scale.

The oxiranes which can be prepared by the process according to the invention are defined by the formula (I). In this formula, X represents oxygen or the CH$_2$ group and Y represents chlorine or phenyl. The radical Z preferably represents hydrogen, fluorine or chlorine.

When, in addition to dimethyl sulphide and methyl bromide, in the process according to the invention 1-(4-chlorophenyl)-4,4-dimethyl-3-pentanone is used as the starting material and potassium tert.-butylate is used as the base, then the course of the reaction can be illustrated by the diagram below:

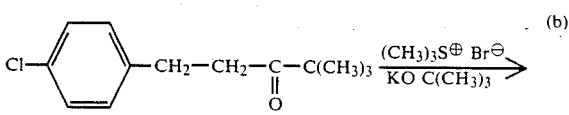

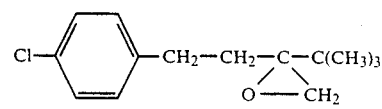

The ketones necessary as starting materials for the process according to the invention are defined by the formula (III). In this formula, Y represents chlorine or phenyl and X represents oxygen or the CH$_2$ group. The radical Z preferably represents hydrogen, fluorine or chlorine.

The ketones of the formula (III) are known (compare German Patent Specification 2,201,063, DE-OS (German Published Specification) 2,705,678 and DE-OS (German Published Specification) 2,737,489).

The trimethylsulphonium bromide of the formula (II) which is also necessary as a starting material for the process according to the invention is likewise known (compare Ber. 96, 1881–1890 (1963)). It is used in the above reaction in the freshly prepared state, optionally without previous isolation.

Strong inorganic and organic bases can be used as bases in the process according to the invention. Suitable and preferred are sodium hydride, sodium amide, also alkali metal alcoholates, such as sodium methylate, sodium ethylate and potassium tert,-butylate, in addition to alkali metal hydroxides, such as potassium hydroxide and sodium hydroxide.

All inert organic solvents can be used as the diluent for the process according tot he invention, both for the preparation of the trimethylsulphonium bromide and for the subsequent reaction of the material with a ketone of the formula (III). Suitable and preferable solvents for the reaction of dimethyl sulphide and methyl bromide are nitriles, such as acetonitrile, or low boiling ketones, such as acetone. Solvents suitable for the subsequent reaction of the trimethylsulphonium bromide with a ketone of the formula (III) are nitriles, such as acetonitrile, also polar solvents, such as dimethyl sulphoxide, and furthermore aromatic or aliphatic hydrocarbons, such as hexane, benzene, toluene and xylene, and moreover alcohols, such as isopropanol and tert.butanol. It is also possible to use mixtures of these solvents.

On carrying out the process according to the invention, the reaction temperatures can be varied within a certain range. In general, both for the preparation of the trimethylsulphonium bromide and for its subsequent reaction with a ketone of the formula (III), temperatures between 0° C. and 60° C., preferably between 10° C. and 40° C., are used.

The process according to the invention is generally carried out under normal pressure. However, it is also possible to carry it out under elevated or reduced pressure.

In carrying out the process according to the invention, in the first step dimethyl sulphide is reacted with an equivalent amount or with an excess of methyl bromide. In the second step, the amounts of the components in the reaction are generally selected such that 1.0 to 2.0 moles, preferably 1.1 to 1.5 moles, of trimethylsulphonium bromide and 1.0 to 2.0 moles, preferably 1.0 to 1.5 moles, of base are present per mole of ketone of the formula (III).

The specific procedure for carrying out the process according to the invention is such that methyl bromide is passed into a solution of dimethyl sulphide in an organic solvent and then the resulting salt is either added after previous isolation or directly to a mixture of the ketone of the formula (III) and the base in an organic solvent. The working up is by customary methods. In general, the procedure is such that an oxidizing agent, such as, for example, an aqueous hydrogen peroxide solution or a mixture of dilute aqueous sodium hypochlorite or potassium hypochlorite solution, and a solvent which is poorly miscible with water and water are added to the reaction mixture, and the organic phase is separated off, washed and evaporated after previous drying if necessary.

The product resulting thereby can be distilled under reduced pressure for further purification.

The oxiranes of the formula (I) which can be prepared by the process according to the invention are valuable starting materials for the synthesis of 1-hydroxyethylazole derivatives which have outstanding plant-growth regulating and fungicidal properties (compare EP-OS (European Published Specification) 40,345).

Thus, for example, 1-(4-chlorophenyl)-4,4-dimethyl-3-(1,2,4-triazol-1-ylmethyl)-3-pentanol of the formula

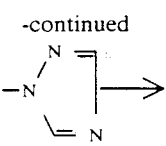

can be prepared by reacting 2-(4-chlorophenylethyl)-2tert.-butyloxirane with 1,2,4-triazole in the presence of potassium hydroxide. This synthesis can be illustrated by the formulae below:

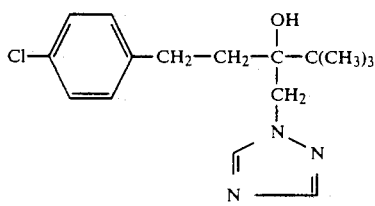

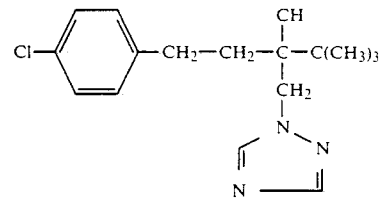

The process according to the invention is illustrated by the examples which follow.

EXAMPLE 1

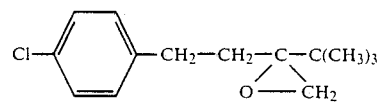

95 g (1 mole) of methyl bromide were passed into a solution of 62 g (1 mole) of dimethyl sulphide in 300 ml of acetone at 20° C. within 4 hours. The mixture was allowed to stir for 10 hours, and then the precipitated trimethylsulphonium bromide was filtered off with suction and the salt was dried at 30° C. 115 g (73% of theory) of trimethylsulphonium bromide were obtained in this manner.

22.4 g (0.1 mole) of 1-(4-chlorophenyl)-4,4-dimethyl-3-pentanone were added to a mixture of 22.4 g (0.2 mole) of potassium tert.-butylate in 100 ml of tert.-butanol at room temperature with stirring. Then 23.5 g (0.15 mole) of trimethylsulphonium bromide were added, whereupon the temperature of the reaction mixture rose to 30° C. Quantitative conversion was achieved after stirring at room temperature for 22 hours. According to analysis by gas chromatography, the content of the desired final product was 98.8%. For work-up, 200 ml of water and 20 ml of aqueous sodium hypochlorite solution were added consecutively to the reaction mixture. It was then extracted with a total of 250 ml of ethylene chloride, and the organic phase was washed with water to neutrality and then concentrated by removing the solvent under reduced pressure. An oily residue weighing 21.1 g remained, which consisted of 95.9% of 2-(4-chlorophenylethyl)-2-tert.-butyloxirane according to the gas chromatogram. A yield of 84.8% of theory is calculated from this.

Comparison example

Preparation of 2-(4-chlorophenylethyl)-2-tert.-butyloxirane of the formula

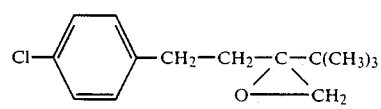

by a known process.

A solution of 108 ml (1.47 mole) of dimethyl sulphide in 130 ml of acetonitrile was added dropwise, with stirring, to a solution of 126 ml (1.33 mole) of dimethyl sulphate in 670 ml of acetonitrile. The reaction mixture was allowed to stand overnight and then 79.2 g (1.47 mole) of solid powdered sodium methylate were added, the temperature of the reaction mixture being maintained at about 20° C. Then a solution of 179 g (0.8 mole) of 1-(4-chlorophenyl)-4,4-dimethyl-3-pentanone in 250 ml of acetonitrile was added dropwise. The reaction mixture was stirred for 4 hours and then allowed to stand overnight. The reaction mixture was then concentrated under reduced pressure, and the remaining residue was dissolved in ethyl acetate. The solution produced thereby was washed with water and, after drying over sodium sulphate, was concentrated by removing the solvent under reduced pressure.

The residue remaining was subjected to vacuum distillation. 157 g of a product which had a boiling point of 102°–105° C. at 0.01 mbar and which, according to the gas chromatogram, consisted of 53% of 2-(4-chlorophenylethyl)-2-tert.-butyloxirane were obtained in this manner. A yield of 43% of theory was calculated from this. Example for the use of an oxirane which can be prepared according to the invention for the synthesis of a -hydroxyethylazole derivative having plant-growth regulating and fungicidal activity

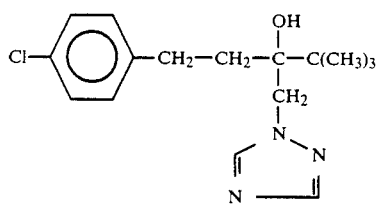

A solution of 27.1 g (0.1 mole) of a product which consisted of 88% of 2-(4-chlorophenylethyl)-2-tert.-butyloxirane, 8.3 g (0.12 mole) of 1,2,4-triazole and 0.06 g (0.01 mole) of potassium hydroxide in 100 ml of n-propanol was heated at 95° C. for 30 hours. It was then allowed to cool and the reaction mixture was concentrated by removing the solvent under reduced pressure. The residue remaining was taken up in toluene, the suspension produced thereby was filtered and the filtrate was concentrated by removing the solvent under reduced pressure. The resulting residue was recrystallized from ligroin. 30.6 g of a product which, according to HPLC analysis, consisted of 67.4% of 1-(4-chlorophenyl)-4,4-dimethyl-3-(1,2,4-triazol-1-ylmethyl)-3-pentanol were obtained in this manner. A yield of 67% of theory was calculated from this.

It will be appreciated that the instant specification and examples are set forth by way of illustration and not limitation, and that various modifications and changes may be made without departing from the spirit and scope of the present invention.

We claim:

1. A process for the preparation of an oxirane of the formula

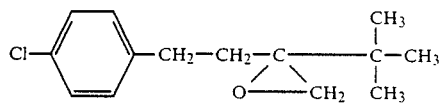

comprising reacting dimethyl sulphide with methyl bromide in the presence of acetone thereby to produce trimethylsulphonium bromide of the formula

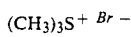

and reacting the trimethylsulphonium bromide with 1-(4-chlorophenyl)-4,4-dimethyl-3-pentanone in the presence of potassium tert.-butylate and in the presence of tert.-butanol, at a temperature between about 10° C. and 40° C., 1.0 to 2.0 moles of trimethylsulphonium bromide and 1.0 to 2.0 moles of potassium tert.-butylate being present per mole of said 1-(4-chlorophenyl)4,4-dimethyl-3-pentanone.

2. A process according to claim 1, wherein said process is carried out under normal pressure.

3. A process according to claim 1, wherein said process is carried out under elevated pressure.

4. A process according to claim 1, wherein said process is carried out under reduced pressure.

5. A process according to claim 1, wherein said dimethyl sulphide is reacted with an equivalent amount of methyl bromide.

6. A process according to claim 1, wherein said dimethyl sulphide is reacted with an excess of methyl bromide.

7. A process according to claim 1, wherein 1.1 to 1.5 moles of trimethylsulphonium bromide and 1.0 to 1.5 moles of potassium tert.-butylate are present per mole of said 1-(4-chlorophenyl)-4,4-dimethyl-3-pentanone.

8. A process according to claim 1, wherein said methyl bromide is passed into a solution of dimethyl sulphide in said acetone and the resulting salt is added after previous isolation or directly into a mixture of 1-(4-chlorophenyl)-4 4-dimethyl-3pentanone and said potassium tert.-butylate in said second inert organic diluent.

9. The process according to claim 1, wherein the preparation of the trimethylsulphonium bromide and its subsequent reaction are effected in two steps.

* * * * *